United States Patent [19]

Shiraki et al.

[11] Patent Number: 4,783,573

[45] Date of Patent: Nov. 8, 1988

[54] PROCESS FOR PREPARING LINEAR α-OLEFINS

[75] Inventors: Yasushi Shiraki; Shinichi Kawano; Kunio Takeuchi, all of Tokuyama, Japan

[73] Assignee: Idemitsu Petrochemical Company Limited, Tokyo, Japan

[21] Appl. No.: 946,218

[22] Filed: Dec. 24, 1986

[30] Foreign Application Priority Data

Apr. 17, 1986 [JP] Japan .................................. 61-88863
Aug. 6, 1986 [JP] Japan ................................. 61-184700

[51] Int. Cl.$^4$ ............................................... C07C 2/02
[52] U.S. Cl. ..................................... 585/523; 585/511
[58] Field of Search ................................ 585/523, 511

[56] References Cited

U.S. PATENT DOCUMENTS 4,486,615 12/1984 Langer ................................. 585/523

Primary Examiner—Curtis R. Davis
Attorney, Agent, or Firm—Armstrong, Nikaido, Marmelstein & Kubovcik

[57] ABSTRACT

A process for preparing a linear α-olefin having from 4 to 20 carbon atoms is disclosed which comprises polymerizing ethylene or gas containing ethylene in the presence of a catalyst consisting of a zirconium halide, an organoaluminium compound and a Lewis base, and adding a catalyst deactivating agent to the resulting reaction mixture, wherein said Lewis base is at least one member selected from the group consisting of thioethers, alkyl disulfides, thiophenes, thiourea, sulfides, phosphines and primary amines.

Use of the catalyst enables preparation of linear α-olefins of a high purity and reduction in the amount of by-produced wax.

6 Claims, No Drawings

PROCESS FOR PREPARING LINEAR α-OLEFINS

FIELD OF THE INVENTION

The present invention relates to a process for preparing linear α-olefins. More particularly, the present invention relates to a process for preparing α-olefins by oligomerizing ethylene according to which not only linear α-olefins can be prepared in high purities with by-producing wax in small amounts but also long production run is possible.

BACKGROUND OF THE INVENTION

α-Olefins are useful as a comonomer for modification in the field of preparing polyolefins or as a plasticizer or a surface active agent after they are alcoholized.

Generally, such linear α-olefins are prepared by oligomerizing ethylene in the presence of a catalyst. As for the catalyst there is known, for example, a binary catalyst which consists of titanium tetrachloride and ethylaluminium dichloride. Also, a process for increasing the yield and selectivity of α-olefins using a catalyst which consists of a third component in addition to the above-described binary catalyst composition is known.

On the other hand, binary catalysts with increased activities have recently been proposed which comprises zirconium (Zr) instead of the above-described titanium compound. For example, Japanese Patent Application Laid-Open Nos. 109428/83, 201729/83 and 113138/83 and Japanese Patent Publication No. 30042/75 disclose binary catalysts whcih consist of a Zr compound and an Al compound.

However, processes for the oligomerization of ethylene using the above-described binary catalysts comprising Zr have caused various problems. For example, final products contain wax fraction in large amounts or the yield of oligomers having a small number of carbon atoms, e.g., those having about 4 carbon atoms, is increased and the purity of the α-olefins obtained is very low. Further, long continuous operation of production unit is difficult since wax fraction is formed in a large amount or for other reasons.

U.S. Pat. No. 4,486,615 discloses a catalyst composition consisting of a binary catalyst composed of a Zr compound and an Al compound and a Lewis base such as a tertiary amine, a secondary amine, an ether, a phosphine oxide, an alkyl phosphate, an aryl phosphate, a sulfoxide, etc. which is added as a third component in order to increase the activity of the binary catalyst.

However, although it is described in U.S. Pat. No. 4,486,615 that a linear α-olefin having high purity as high as 99.5% can be prepared using the catalyst composition containing triethylamine as the most preferred example of the Lewis base it has been confirmed by the present inventors that use of the catalyst compositions containing Lewis bases referred to in U.S. Pat. No. 4,486,615 other than triethylamine results in the preparation of linear α-olefins having low purity and that a large amount of the above-described ternary catalyst containing triethylamine is used in U.S. Pat. No. 4,486,615.

SUMMARY OF THE INVENTION

An object of the present invention is to obviate the defects of the conventional processes and to provide a process for preparing a linear α-olefin by oligomerizing ethylene according to which the medium fraction containing from about 6 to 20 carbon atoms can be obtained in a high yield and the purity of the α-olefin obtained is high with forming a small amount of wax fraction, thus enabling long production runs.

Another object of the present invention is to provide a process for preparing a linear α-olefin by oligomerizing ethylene according to which linear α-olefins containing low content of halogen derived from the catalyst used can be prepared in high purity.

In order to achieve the above objects extensive investigations have been carried out by the present inventors and as a result it has now been found that excellent effects are obtained by the use of a novel ternary catalyst which consists of a Zr compound, an Al compound and a specified third component. The present invention is based on this discovery.

That is, the present invention provides a process for preparing a linear α-olefin having from 4 to 20 carbon atoms comprising polymerizing ethylene or gas containing ethylene in the presence of a catalyst consisting of a zirconium halide, an organoaluminium compound and a Lewis base, and adding a catalyst deactivator to the resulting reaction mixture wherein said Lewis base is at least one member selected from the group consisting of thioethers, alkyl disulfides, thiophenes, thiourea, sulfides, phosphines and primary amines.

DETAILED DESCRIPTION OF THE INVENTION

In the process of the present invention, a novel ternary catalyst is used which consists of a zirconium halide (hereinafter, sometimes referred to as "Component A"), the above-described organoaluminium compound (hereinafter, sometimes referred to as "Component B") and a Lewis base specified hereinbelow (hereinafter, sometimes referred to as "Component C").

The zirconium halide used as Component A is a compound represented by formula (I) below $$ZrX_aA_{4-a} \tag{I}$$

wherein X and A, which may be the same or different, each represents Cl, Br or I, and a is 0 or an integer of up to 4.

Specific examples of the zirconium halide represented by the formula (I) include $ZrCl_4$, $ZrBr_4$, $ZrI_4$, $ZrBrCl_3$, $ZrBr_2Cl$, etc. Among these, $ZrCl_4$ is particularly preferred. They can be used singly or two or more of them can be used in combination.

The organoaluminium compound which can be used in the present invention is an alkylaluminium sesquihalide represented by formula (II) below $$AlR_{1.5}Q_{1.5} \tag{II}$$

wherein R represents an alkyl group having from 1 to 20 carbon atoms, and Q represents Cl, Br or I (formula (II) may also be expressed as $Al_2R_3Q_3$) or an alkylaluminium compound represented by formula (III) below $$AlR'_bQ'_{3-b} \tag{III}$$

wherein R' and Q', which may be the same or different, have the same meanings as R and Q in formula (II), and b is an integer of 1 to 3.

The alkylaluminium sesquihalide represented by formula (II) above which can be used as Component B (hereinafter, sometimes referred to as "Component B-1") is not limited particularly as far as R and Q in formula (II) satisfy the above-described conditions. Specific examples thereof include $Al_2(CH_3)_3Cl_3$, $Al_2(CH_3)_3Br_3$, $Al_2(C_2H_5)_3Cl_3$, $Al_2(C_2H_6)_3Br_3$, $Al_2(C_2H_5)_3I_3$, $Al_2(C_2H_6)_3BrCl_2$, $Al_2(C_3H_7)_3Cl_3$, $Al_2$-(iso-$C_3H_7)_3Cl_3$, $Al_2(C_4H_3)_3Cl_3$, $Al_2(iso-C_4H_9)_3Cl_3$, $Al_2(C_5H_{11})_3Cl_3$, $Al_2(C_8H_{17})_3Cl_3$, $Al_2(C_2H_5)_2(CH_8)Cl_8$, etc.

Among these, compounds in which R represents a methyl group, an ethyl group, a propyl group or a butyl group are preferred and those in which R represents an ethyl group are particularly preferred.

It is preferred that Q represents Cl.

Specifically, ethylaluminium sesquichloride $(Al(C_2H_5)_{1.5}Cl_{1.5}$, i.e., $Al_2(C_2H_6)_3Cl_3)$ is preferred.

These alkylaluminium sesquihalides can be used singly or two or more of them can be used in combination.

The alkylaluminium compound represented by formula (III) above which can be used as Component B (hereinafter, sometimes referred to as "Component B-2") is not limited particularly as far as R' and Q' in formula (II) satisfy the above-described conditions. Specific examples thereof include $Al_3(CH_3)_3$, $Al(C_2H_5)_3$, $Al(C_3H_7)_0$, $Al(iso—C_3H_7)$, $Al-(C_4H_0)_3$, $Al-$(iso—$C_4H_9)_3$, $Al(C_6H_{11})_3$, $Al(C_6H_{13})_3$, $Al(C_8H_{17})_3$, $Al(C_2H_5)_2Cl$, $Al(C_2H_5)_2Br$, $Al(C_2H_5)_2I$, $Al(C_2H_5)Cl_2$, $Al(C_2H_5)$-$Br_2$, $Al(C_2H_5)I_2$, etc.

However, among the compounds represented by formula (III), those in which b is 2 or 3 are preferred.

In formula (III), R' is preferably an ethyl group, a propyl group, a butyl group or an isobutyl group and more preferably an ethyl group.

It is preferred that Q' represents Cl.

Specifically, compounds such as triethylaluminium, diethylaluminium chloride and ethylaluminium dichloride are preferred.

These alkylaluminium compounds can be used singly or two or more of them can be used in combination as Component B-2.

The Lewis base which can be used as Component C is at least one member selected from the group consisting of thioethers, alkyldisulfides, thiophenes, thiourea, sulfides, phosphines and primary amines.

As for the thioethers, there can be cited, for example, dimethyl sulfide, dipropyl sulfide, dihexyl sulfide, dicyclohexyl sulfide, diphenyl thioether, etc.

As for the alkyl disulfides, there can be cited, for example, methyl disulfide ($(CH_3)_2S_2$), ethyl disulfide, propyl disulfide, butyl disulfide, hexyl disulfide, cyclohexyl disulfide, ethyl methyl disulfide, etc.

As for the thiophenes, there can be cited, for example, thiophene, 2-methylthiophene, 3-methylthiophene, 2,3-dimethylthiophene, 2-ethylthiophene, benzothiophene, tetrahydrothiophene, etc.

As for the sulfides, there can be cited, for example, methyl sulfide, ethyl sulfide, butyl sulfide, etc.

As for the phosphines, there can be cited, for example, triphenylphosphine, triethylphosphine, tributylphosphine, tripropylphosphine, trioctylphosphine, tricyclohexylphosphine, etc.

As for the primary amines, there can be cited, for example, organic amines such as methylamine, ethylamine, propylamine, butylamine, pentylamine, hexylamine, cyclohexylamine, octylamine, decylamine, aniline, benzylamine, naphthylamine, trimethylamine, triethylamine, tributylamine, triphenylamine, pyridine, picoline, etc.

These compounds can be used singly or two or more of them can be used in combination.

Among the various Lewis bases defined in the present invention, at least one member selected from the group consisting of methyl disulfide, thiophene, thiourea, triphenylphosphine, trioctylphosphine and aniline can be used particularly advantageously.

In the process of the present invention, compounds belonging to Components A, B and C, respectively, can be selected appropriately and the selected compounds are combined to prepare a catalyst which can be used to achieve the objects of the present invention.

However, a catalyst which is obtained by selecting a mixture of Component B-1 and Component B-2 as Component B and combining the mixture with Component A and Component C, and a catalyst obtained by combining Component A, Component B-1 and Component C are preferred. More particularly, a catalyst consisting of a mixture of an alkylaluminium sesquihalide and a trialkylaluminium, zirconium tetrachloride and thiophene, and a catalyst consisting of an alkylaluminium sesquihalide, zirconium tetrachloride and thiophene are preferred. This is because when these catalysts are used not only the content of wax in the product of oligomerization reaction can be further reduced but also the yield of linear α-olefins per weight of zirconium halide can be increased and the purity of the linear α-olefin obtained can be increased.

When a mixture of Component B-1 and Component B-2 is used as a catalyst component Component B-1 and Component B-2 are mixed desirably in a proportion such that Component B-2 is not higher than 50 mol% (Al basis), preferably not higher than 30 mol% (Al basis).

In the present invention, there is no particular limitation on the method of preparing catalysts from Components A, B and C. However, it is preferred to contact Component A with Component B in a suitable solvent to form a catalyst preparation liquor which contain a catalyst precursor and then mix this catalyst preparation liquor with Component C upon or prior to the polymerization (oligomerization) of ethylene to obtain a catalyst liquor.

Upon preparation of the catalyst preparation liquor or catalyst liquor, it is desirable that the mixture is heated at a suitable temperature (usually, a temperature lower than the temperature of polymerization reaction, for example, and more specifically within the range of from 60° to 80° C.) for from 10 to 120 minutes to activate the catalyst.

As for the solvent which can usually be used in the present invention, there can be cited, for example, aromatic hydrocarbons and halogenated derivatives thereof such as benzene, toluene, xylene, chlorobenzene, ethylbenzene, dichlorobenzene, chlorotoluene, etc., paraffins such as pentane, hexane, heptane, octane, nonane, decane, etc., naphthenes such as cyclohexane, decaline, etc., haloalkanes such as dichloroethane, dichlorobutane, etc., and the like. Among these, benzene, toluene, xylene and chlorobenzene are preferred with benzene being particularly preferred.

These solvents can be used singly or two or more of them can be used in combination.

In the present invention, the proportion of Components A, B and C mixed per 250 ml of the solvent is usually from 0.005 to 5 mmol and preferably from 0.01 to 1 mmol, of Component A, usually from 0.02 to 15 mmol and preferably from 0.05 to 3 mmol, of Component B, and usually from 0.01 to 20 mmol and preferably from 0.02 to 20 mmol, of Component C when sulfur compounds (thioethers, alkyl disulfides, thiophenes, thiourea and sulfides) are used or from 0.01 to 5 mmol of Component C when phosphines or primary amines are used. As for the proportion of Components A and B, more desirable results can be obtained by setting the proportion of Al/Zr by mole within the range of from 1 to 15.

Upon polymerization, the catalyst liquor can be mixed with the solvent to adjust the concentration of the catalyst, if desired.

The thus prepared catalyst or catalyst liquor and ethylene or a gas containing ethylene are contacted in the above-described solvent at a predetermined reaction temperature under a predetermined reaction pressure to carry out polymerization (oligomerization) of ethylene efficiently.

The gas containing ethylene which can be used in the present invention include an inert gas containing ethylene, purified ethylene gas for polymerization, ethylene gas for polymerization such as high purity ethylene, etc., with high purity ethylene being preferred.

The reaction temperature upon polymerization is usually from 50° to 200° C., preferably from 100° to 150° C. The reaction pressure is usually not lower than 5 Kg/cm$^2$ (gauge pressure), preferably not lower than 25 Kg/cm$^2$ (gauge pressure). The reaction time is usually from about 5 minutes to about 2 hours, preferably from about 15 minutes to about 1 hour.

All the operations starting from the preparation of the catalyst to the completion of the polymerization reaction are desirably carried out in the absence of air and moisture.

It is preferred that the preparation of the catalyst is carried out under the atmosphere of an inert gas such as nitrogen, argon, etc.

Further, it is desirable that starting materials for preparing the catalyst, solvent and starting materials for polymerization are dried sufficiently. However, copresence of a minute amount of moisture or air sometimes results in increase in the activity and selectivity of the catalyst.

Hereinafter, example of the process for preparing linear α-olefins according to the present invention will be described in detail.

That is, in a vessel equipped with a stirrer there are dissolved Component A, e.g., zirconium tetrachloride, and Component B, e.g., ethylaluminium sesquichloride, in the solvent, e.g., benzene, under the atmosphere of the inert gas, e.g., argon, nitrogen, etc., and heated at a temperature of from 60° to 80° C. for from 10 to 120 minutes with stirring to prepare a catalyst preparation liquor.

A portion of the catalyst preparation liquor thus obtained is transferred to another vessel equipped with a stirrer under the atmosphere of the inert gas and diluted with the solvent, e.g., benzene, and then Component C, e.g., thiophene, is added thereto at a temperature in the vicinity of room temperature followed by stirring to prepare a catalyst liquor. As a result of the preparation of the catalyst in this manner a complex catalyst derived from a zirconium halide such as zirconium tetrachloride and an alkylaluminium compound is formed, and use of the complex catalyst results in increase in the yield and purity of the objective product, linear α-olefins.

Then, the above-described catalyst liquor is pressed into a reaction vessel kept at a temperature of from 50° to 60° C. under the atmosphere of an inert gas, and while stirring the catalyst liquor a gas containing ethylene such as high purity ethylene is introduced followed by oligomerizing ethylene under the above-described reaction conditions.

After a predetermined period of time a conventional catalyst deactivating agent such as an aqueous alkali solution or an aqueous methanol solution containing an alkali can be added to the reaction mixture to terminate the reaction.

As for the catalyst deactivating agent, there can be cited, for example, water, alcohols (monohydric alcohols, polyhydric alcohols, cyclic alcohols, acyclic alcohols, aliphatic alcohols, aromatic alcohols), carboxylic acids, phenols, etc.

When the catalysts is deactivated it is preferred to add a nitrogen containing compound in addition to the catalyst deactivating agent described above to the reaction mixture since addition of halogen derived from the catalyst to the resulting linear α-olefin can be prevented by the addition of the nitrogen containing compound, thus further improving the purity of the linear α-olefin.

As for the nitrogen containing compounds, there can be cited, for example, ammonia or amines such as methylamine, ethylamine, propylamine, butylamine, pentylamine, hexylamine, cyclohexylamine, octylamine, decylamine, aniline, benzylamine, naphthylamine, dimethylamine, diethylamine, dibutylamine, diphonylamine, methylphenylamine, trimethylamine, triethylamine, tributylamine, triphenylamine, pyridine, picoline, etc.

These nitrogen containing compounds can be used singly or two or more of them can be used in combination.

The order of adding the deactivating agent and the nitrogen containing compound to the reaction mixture is not limited particularly. For example, the order of addition may be (1) first to add the nitrogen containing compound and then the deactivating agent, (2) first to add the deactivating agent and then the nitrogen containing compound or (3) to simultaneously add the nitrogen containing compound and the deactivating agent.

Of the above orders of addition, the order (1) is preferred.

After deactivation of the catalyst in the abovedescribed manner the resulting product liquor contains high content of linear α-olefins which have from about 6 to about 44 carbon atoms, particularly from 6 to 20 carbon atoms in good yield and which do not contain halogen. On the other hand, by-production of wax component is remarkably reduced.

The reaction product liquor after deactivation of the catalyst can be subjected to post-treatments, e.g., washing with water, etc., separation such as extraction, filtration, etc., drying and the like to recover the objective products, e.g., linear α-olefins of high purity in high efficiency.

That is, according to the process of the present invention, linear α-olefins of such high purity that they contain from about 6 to about 22 carbon atoms can be obtained stably in high yield. And linear α-olefins having from about 6 to about 20 carbon atoms can be obtained at high selectivity. It is possible to control the carbon atom number distribution of the product to a further narrow range by appropriately selecting the reaction conditions, catalyst composition, concentration, etc.

The unused ethylene or a low boiling point fraction containing unused ethylene which is recovered may be used as it is or recycled after purification for use as a starting material for the reaction.

The linear α-olefins prepared according to the process of the present invention can be used advantageously as a comonomer for preparing various copolymers and also employed in various fields of industry such as plasticizers, and starting materials for preparing surface acitve agents.

According to the present invention, the following effects can be obtained.

That is, in the process of the present invention, use of the catalyst prepared from a zirconium halide, an organoaluminium compound and a specified Lewis base enables preparation of linear α-olefins of high purity and reduction in the amount of by-produced wax.

More particularly, the catalysts prepared from zirconium tetrachloride (A), alkylaluminium sesquihalide (B-1) or a mixture of alkylaluminium sesquihalide (B-1) and alkylaluminium halide (B-2), particularly trialkylaluminium halide, and at least one Lewis base (C) selected from the group consisting of thioethers, alkyl disulfides, thiophenes, thiourea, sulfides, phosphines and primary amines have a high activity, and when these catalysts are used linear α-olefins of higher purity can be prepared, the amount of wax by-produced can be reduced further, and the yield of linear α-olefins based on the zirconium tetrachloride can be increased.

Further, in the process of the present invention, addition of a nitrogen containing compound upon deactivation of the catalyst in the resulting polymerization reaction product liquor obtained by oligomerization of ethylene the content of halogen in the linear α-olefins can be reduced and linear α-olefins of higher purity can be prepared.

In addition, when the reaction is carried out at high temperatures by-production of wax component is in a small amount and therefore operational performance of the process is improved greatly, thus enabling long production runs.

EXAMPLES

The present invention will be described in greater detail with reference to the following examples and comparative examples.

EXAMPLES 1–15

Preparation Example of Catalyst (Preparation of Catalyst Liquor)

In a 1,000 ml flask equipped with a stirrer were introduced 50 mmol of anhydrous zirconium tetrachloride and 472 ml of dry benzene under the atmosphere of argon and the resulting mixture was stirred for 30 minutes. To the mixture was added the alkylaluminium compound shown in Table 1 in such an amount that it occupies a molar ratio to zirconium tetrachloride calculated from the amount indicated in Table 1 (for example, in Examples 1 to 4 and 6 to 10 the molar ratio of $Al_2(C_2H_6)_3Cl_3/ZrCl_4$ is 5.0 and therefore 250 mmol of ethylaluminium sesquichloride was added), and the mixture was stirred at 60° C. for 30 minutes to obtain a catalyst preparation liquor.

Then, in a 500 ml three-neck flask were introduced dry benzene and the catalyst preparation liquor in predetermined amounts, respectively, under the atmosphere of argon, followed by adjusting the amounts of zirconium tetrachloride, the ethylaluminium compound indicated and benzene to the values indicated in Table 1. To the resulting mixture was added a predetermined amount of the third component (thiophene, aniline, thiourea, triphenylphosphine or trioctylphosphine) and the mixture was stirred at room temperature for 10 minutes to obtain a catalyst liquor.

Preparation Example of α-Olefin (Oligomerization of Ethylene)

In a 1 liter autoclave equipped with a stirrer was introduced the catalyst liquor prepared in the abovedescribed preparation example of catalyst by conveying using pressurized argon under the atmosphere of dry argon. The temperature of the autoclave was kept at 50° to 60° C. After the charging of the catalyst liquor was over stirring was started and high purity ethylene gas was introduced rapidly into the autoclave and charging was continued until the inside pressure reached the reaction pressure indicated in Table 1 and then the temperature was elevated to the reaction temperature indicated in Table 1. Introduction of ethylene was continued in an amount necessary to maintain the reaction pressure. After the reaction was continued for 1 hour with maintaining the reaction conditions an aqueous solution of sodium hydroxide was pressed into the autoclave to deactivate the catalyst and thus terminate the reaction. Then, the following post-treatments were carried out.

At first, 20 g of undecane for use as an internal standard for chromatography was added to the reaction product and then wax component was filtered out using a filter paper. The wax component on the filter paper was washed sufficiently with benzene to drip down light fraction in the filtrate. The product in the filtrate was washed twice with 500 ml of deionized water and dried over anhydrous potassium carbonate.

The thus-obained transparent solution of the reaction product was analyzed by gas chromatography. The yield of the product was obtained by internal standard method.

On the other hand, the wax component which was filtered out was weighed after it was air dried and then dried in a vacuum drier at a pressure of 20 mmHg.

The yield of C4 to C8 fractions was calculated from the Schultz-Flory distribution since operational loss could not be avoided.

The results obtained are shown in Table 1.

COMPARATIVE EXAMPLES 1–5

The same procedures as in Example 1 were repeated except that as shown in Table 1, at least one of zirconium tetrachloride, ethylaluminium sesquichloride and the third component was omitted. And the amount of each component used and the reaction conditions are as indicated in Table 1. The results contained are shown in Table 1.

TABLE 1

| | Unit | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 | Ex. 13 | Ex. 14 | Ex. 15 | C. Ex. 1 | C. Ex. 2 | C. Ex. 3 | C. Ex. 4 | C. Ex. 5 |
|---|---|---|---|---|---|---|---|---|---|---|---|---|---|---|---|---|---|---|---|---|---|
| Catalyst Composition | | | | | | | | | | | | | | | | | | | | | |
| $ZrCl_4$ | mmol | 1.0 | 0.2 | 0.2 | 0.2 | 0.2 | 0.2 | 0.2 | 0.2 | 0.2 | 0.2 | 0.1 | 0.2 | 0.1 | 0.05 | 0.05 | 0.2 | 0.1 | — | 0.1 | — |
| $EASC^1$ | mmol | 5.0 | 1.0 | 1.0 | 1.0 | 0.5 | 1.0 | 1.0 | 1.0 | 1.0 | 1.0 | 0.47 | 0.93 | 0.38 | 0.38 | 0.33 | 1.0 | — | 1.0 | — | — |
| $DEAC^2$ | mmol | — | — | — | — | — | — | — | — | — | — | 0.02 | 0.05 | — | — | — | — | 0.5 | — | 0.125 | 0.5 |
| $TEA^3$ | mmol | 2.0 | 0.4 | 1.2 | — | 0.4 | — | — | — | — | — | 0.2 | 0.4 | 0.08 | 0.08 | 0.11 | — | 0.2 | — | 0.125 | — |
| Thiophene | mmol | — | — | — | — | — | 0.08 | 0.3 | — | — | — | — | — | 0.2 | 0.3 | 0.3 | — | — | — | 0.2 | — |
| $MDS^4$ | mmol | — | — | — | — | — | — | — | 0.6 | — | — | — | — | — | — | — | — | — | — | — | — |
| Aniline | mmol | — | — | — | — | — | — | — | — | 0.4 | — | — | — | — | — | — | — | — | — | — | — |
| Thiourea | mmol | — | — | — | — | — | — | — | — | — | 0.25 | — | — | — | — | — | — | — | — | — | — |
| $TPP^6$ | mmol | — | — | — | — | — | — | — | — | — | — | — | — | — | — | — | — | — | — | — | — |
| $TOP^{11}$ | mmol | — | — | — | — | — | — | — | — | — | — | — | — | — | — | — | — | — | — | — | — |
| Al/Zr | mol/mol | 5.0 | 5.0 | 5.0 | 5.0 | 2.5 | 5.0 | 5.0 | 5.0 | 5.0 | 5.0 | 4.9 | 4.9 | 4.6 | 9.2 | 8.8 | 5.0 | 5.0 | 8 | 2.5 | 8 |
| Benzene | ml | 250 | 250 | 250 | 250 | 250 | 250 | 250 | 250 | 250 | 250 | 250 | 250 | 250 | 250 | 250 | 250 | 250 | 250 | — | 250 |
| Reaction Condition | | | | | | | | | | | | | | | | | | | | | |
| Temperature | °C | 100 | 120 | 120 | 120 | 120 | 120 | 120 | 120 | 120 | 120 | 120 | 100 | 120 | 120 | 120 | 100 | 120 | 120 | 120 | 120 |
| Pressure | Kg/Cm² G | 35 | 35 | 35 | 45 | 35 | 35 | 35 | 35 | 35 | 35 | 35 | 35 | 35 | 35 | 35 | 35 | 35 | 35 | 35 | 35 |
| Time | min. | 60 | 60 | 60 | 60 | 60 | 60 | 60 | 60 | 60 | 60 | 60 | 60 | 60 | 60 | 60 | 60 | 60 | 60 | 60 | 60 |

| | Example 1 | | Example 2 | | Example 3 | | Example 4 | | Example 5 | | Example 6 | | Example 7 | | Example 8 | | Example 9 | | Example 10 | | Example 11 | | Example 12 | | Example 13 | |
|---|---|---|---|---|---|---|---|---|---|---|---|---|---|---|---|---|---|---|---|---|---|---|---|---|---|---|
| Product | C (wt. %) | P | C (wt. %) | P | C (wt. %) | P | C (wt. %) | P | C (wt. %) | P | C (wt. %) | P | C (wt. %) | P | C (wt. %) | P | C (wt. %) | P | C (wt. %) | P | C (wt. %) | P | C (wt. %) | P | C (wt. %) | P |
| α-Olefin | | | | | | | | | | | | | | | | | | | | | | | | | | |
| $C_4$ | 23.9 | 100 | 9.4 | 100 | 15.2 | 100 | 14.5 | 100 | 9.4 | 100 | 10.7 | 100 | 14.0 | 100 | 15.0 | 100 | 12.2 | 100 | 9.0 | 100 | 9.8 | 100 | 18.2 | 100 | 12.3 | 100 |
| $C_6$ | 21.1 | 99 | 10.6 | 100 | 15.3 | 100 | 14.8 | 100 | 10.4 | 100 | 12.6 | 100 | 13.4 | 100 | 14.5 | 100 | 12.9 | 100 | 9.5 | 99 | 10.8 | 100 | 17.5 | 100 | 13.0 | 100 |
| $C_8$ | 16.9 | 98 | 10.7 | 99 | 14.3 | 100 | 13.4 | 100 | 10.0 | 100 | 13.4 | 100 | 11.7 | 99 | 12.6 | 99 | 12.3 | 98 | 10.9 | 98 | 10.4 | 100 | 15.2 | 100 | 12.0 | 98 |
| $C_{10}$ | 12.2 | 97 | 10.4 | 98 | 12.0 | 100 | 11.9 | 100 | 9.4 | 99 | 12.1 | 100 | 9.5 | 98 | 10.2 | 98 | 11.1 | 97 | 9.7 | 97 | 10.0 | 99 | 12.4 | 99 | 11.3 | 97 |
| $C_{12}$ | 8.6 | 95 | 9.1 | 97 | 9.2 | 99 | 9.3 | 100 | 8.2 | 98 | 9.9 | 99 | 7.1 | 98 | 7.6 | 97 | 8.9 | 96 | 8.9 | 96 | 8.7 | 99 | 9.2 | 99 | 9.2 | 96 |
| $C_{14}$ | 5.6 | 94 | 7.6 | 97 | 6.8 | 99 | 7.0 | 100 | 6.6 | 98 | 7.4 | 98 | 5.1 | 97 | 5.5 | 96 | 6.8 | 96 | 7.9 | 96 | 7.1 | 99 | 7.2 | 99 | 7.2 | 96 |
| $C_{16}$ | 3.8 | 93 | 7.0 | 96 | 5.4 | 98 | 5.8 | 100 | 5.7 | 97 | 6.7 | 98 | 3.7 | 96 | 4.0 | 96 | 5.9 | 95 | 8.3 | 95 | 5.9 | 98 | 4.8 | 99 | 6.1 | 96 |
| $C_{18}$ | 2.8 | 92 | 6.2 | 96 | 4.9 | 97 | 4.7 | 99 | 5.0 | 96 | 6.0 | 97 | 3.1 | 95 | 3.4 | 95 | 5.1 | 94 | 7.3 | 94 | 5.3 | 98 | 4.1 | 98 | 5.1 | 96 |
| $C_{20+}$ | 4.8 | — | 20.2 | — | 13.7 | — | 14.4 | — | 17.3 | — | 15.7 | — | 11.4 | — | 12.1 | — | 15.3 | — | 18.2 | — | 20.4 | — | 11.3 | — | 18.1 | 97 |
| Wax (wt. %) | 0.3 | | 8.8 | | 3.2 | | 4.2 | | 18.0 | | 5.5 | | 21.0 | | 15.0 | | 9.5 | | 10.3 | | 11.6 | | 0.7 | | 5.7 | |
| Yield (g/g·$ZrCl_4$) | 1530 | | 2320 | | 1900 | | 2760 | | 2600 | | 1720 | | 2000 | | 1500 | | 730 | | 1850 | | 3790 | | 2730 | | 4270 | |

| Product | Example 14 | | Example 15 | | C. Ex. 1 | | C. Ex. 2* | | C. Ex. 3** | | C. Ex. 4* | | C. Ex. 5** | |
|---|---|---|---|---|---|---|---|---|---|---|---|---|---|---|
| | C (wt. %) | P | C (wt. %) | P | C (wt. %) | P | C (wt. %) | P | C (wt. %) | P | C (wt. %) | P | C (wt. %) | P |
| α-Olefin | | | | | | | | | | | | | | |
| $C_4$ | 17.9 | 100 | 12.2 | 100 | 10.9 | 100 | | | | | | | | |
| $C_6$ | 17.5 | 100 | 12.9 | 100 | 11.7 | 99 | | | | | | | | |
| $C_8$ | 15.2 | 99 | 14.3 | 98 | 11.4 | 97 | | | | | | | | |
| $C_{10}$ | 12.4 | 98 | 11.8 | 97 | 9.7 | 95 | | | | | | | | |
| $C_{12}$ | 9.0 | 97 | 8.7 | 96 | 8.6 | 92 | | | | | | | | |
| $C_{14}$ | 6.4 | 97 | 6.1 | 95 | 6.8 | 89 | | | | | | | | |
| $C_{16}$ | 5.0 | 96 | 4.8 | 98 | 5.3 | 86 | | | | | | | | |
| $C_{18}$ | 4.0 | 96 | 3.8 | 92 | 5.0 | 85 | | | | | | | | |
| $C_{20+}$ | 11.6 | — | 14.6 | — | 15.5 | — | | | | | | | | |
| Wax (wt. %) | 1.0 | | 1.9 | | 15.1 | | | | | | | | | |

TABLE 1-continued

| Yield (g/g·ZrCl₄) | 11980 | 15620 | 2600 |

¹EASC stands for ethylaluminium sesquichloride.
²DEAC stands for diathylaluminium chloride.
³TEA stands for Triethylaluminium.
⁴MDS stands for methyl disulfide.
⁵TPP stands for triphenylphosphine.
⁶TOP stands for trioctylphosphine.
Notes:
"C" and "P" stand for composition and purity, respectively.
Purity is expressed in terms of wt. % of linear α-olefins in each fraction.
*Only high polymer was synthesized.
**No reaction.

EXAMPLES 16-27

Preparation Example of Catalyst (Preparation of Catalyst Liquor)

The same procedures as in Example 1 were repeated except that the catalyst compositions indicated in Table 2 were used to prepare catalyst preparation liquors.

Then, catalyst liquors were prepared from the catalyst preparation liquors in the same manner as in Example 1.

Preparation Example of α-Olefins (Oligomerization of Ethylene)

Polymerization of ethylene was carried out in the same manner as in Example 1 except that the deactivating agents shown in Table 3 were used and the nitrogen containing compounds shown in Table 3 were added in amounts shown in Table 3 prior to the addition of the deactivating agents, and then the catalyst was deactivated.

Thereafter, the resulting polymerization reaction product liquor after deactivation of the catalyst was washed with water, and the concentration of chloride ion in the oily layer thus obtained (a mixture of benzene as a solvent and linear α-olefin produced) was determined and the chlorine content of the resulting linear α-olefin was obtained. The same post-treatments as in Example 1 were carried out. The results obtained are shown in Table 3.

COMPARATIVE EXAMPLES 6-13

As shown in Table 3, the same procedures as in Examples 16-27 were repeated except that the nitrogen containing compound was not used. The amount of each component and reaction conditions are as shown in Table 3.

The results obtained are shown in Table 3.

TABLE 2

| | Unit | |
|---|---|---|
| Catalyst Composition | | |
| Zirconium tetrachloride | mmol | 0.05 |
| Ethylaluminium sesquichloride | mmol | 0.21 |
| Triethylaluminium | mmol | 0.04 |
| Thiophene | mmol | 0.30 |
| Al/Zr | mol/mol | 5 |
| Benzene | ml | 250 |
| Reaction Condition | | |
| Temperature | °C. | 120 |
| Pressure | Kg/cm² G | 35 |
| Time | min. | 60 |
| Product | Composition | Purity |
| α-Olefin | | |
| $C_4$ | 14.9 | 100 |
| $C_6$ | 15.1 | 100 |
| $C_8$ | 14.0 | 99 |
| $C_{10}$ | 12.3 | 98 |
| $C_{12}$ | 9.7 | 98 |
| $C_{14}$ | 7.2 | 97 |
| $C_{16}$ | 5.8 | 96 |
| $C_{18}$ | 5.2 | 96 |
| $C_{20+}$ | 14.2 | — |
| Wax (wt. %) | 1.6 | |
| Yield (g/g.ZrCl₄) | 10300 | |
| Amount of α-Olefin (g) | 120 | |

TABLE 3

Zirconium tetrachloride: 0.05 mM
Triethylaluminium: 0.04 mM
Ethylaluminium sesquichloride: 0.21 mM

| | Ex. 16 | Ex. 17 | Ex. 18 | Ex. 19 | Ex. 20 | Ex. 21 | Ex. 22 | Ex. 23 | Ex. 24 | Ex. 25 |
|---|---|---|---|---|---|---|---|---|---|---|
| N-Containing Compound | TEA | TEA | TMA | NH₃ | NH₃ aq. (28%) | NH₃ aq. (10%) | NH₃ aq. (10%) | NH₃ aq. (10%) | NH₃ aq. (10%) | NH₃ aq. (28%) |
| Amount (mM) | 14 | 4 | 90 | 10 | 165 | 58 | 29 | 29 | 18 | 165 |
| Temperature (°C.) | 20 | 20 | 20 | 20 | 20 | 20 | 20 | 40 | 40 | 120 |
| Deactivating Agent | Water | Water | Water | Water | Water | Water | Water | Water | Water | Water |
| Amount (g) | 10 | 10 | 10 | 10 | 7 | 9 | 9 | 4 | 4 | 7 |
| Cl Content in Product (ppm) | ≦2 | ≦2 | ≦2 | ≦2 | ≦2 | ≦2 | ≦2 | ≦2 | 4 | 22 |

| | Ex. 26 | Ex. 27 | C. Ex. 6 | C. Ex. 7 | C. Ex. 8 | C. Ex. 9 | C. Ex. 10 | C. Ex. 11 | C. Ex. 12 | C. Ex. 13 |
|---|---|---|---|---|---|---|---|---|---|---|
| N-Containing Compound | N—MP | TEA | — | — | — | | | | | |
| Amount (mM) | 17 | 14 | — | — | — | | | | | |
| Temperature (°C.) | 20 | 20 | 100 | 20 | 20 | 40 | 40 | 40 | 20 | 20 |
| Deactivating Agent | Methanol | Methanol | Water | Water | Water*¹ | Methanol | Methanol*¹ | Butanol | Octanol | Methanol |
| Amount (g) | 10 | 10 | 50 | 50 | 50 | 5 | 5 | 5 | 5 | 5 |
| Cl Content in Product (ppm) | 7 | ≦2 | 200 | 80 | 80 | 50 | 45 | 50 | 50 | 20 |

Notes:
TEA: Triethylamine,
TMA: Trimethylamine,
N—MP: N—Methylpiperidine,
*¹: containing 1% NaOH,
NH₃ aq.: aqueous ammonia,
NH₃: ammonia gas

EXAMPLES 28-36 AND COMPARATIVE EXAMPLES 14-16

Preparation Example of Catalyst (Preparation of Catalyst Liquor)

In a 2 liter autoclave equipped with a stirrer was introduced a slurry solution composed of 100 ml of dry chlorobenzene and a predetermined amount (mmol) of zirconium compounds shown in Table 4 under the atmosphere of dry argon.

On the other hand, aluminium compounds and sulfur compounds or nitrogen compounds shown in Table 4 were added to 150 ml of dry chlorobenzene and the mixture was stirred for 10 minutes and then introduced into the above-described autoclave to obtain a catalyst liquor.

Preparation Example of α-Olefins (Oligomerization of Ethylene)

At first, the catalyst liquor was heated for 1 hour until the temperature reached 100° C. while stirring in the autoclave to effect activation, and at this timing high purity ethylene gas was introduced rapidly into the autoclave and the charging was continued until the pressure reached 35 Kg/cm²-G. Thereafter, introduction of ethylene was continued in amounts necessary for maintaining the pressure. The reaction was continued under these conditions for about 30 minutes and then the catalyst was deactivated by pressing a methanol solution containing sodium hydroxide into the autoclave to terminate the reaction.

In the post-treatment, reaction products having 4 to 6 carbon atoms (C4–C6) were trapped in a dry ice-methanol bath upon depressurizing the autoclave in order to reduce loss of light fractions comprising C4–C6. Other reaction products were treated as follows. That is, at first wax component was filtered out using a filter paper, and then the filtrate was washed twice with 500 ml of deionized water followed by drying over anhydrous potassium carbonate. The transparent solution thus obtained was analyzed by gas chromatography. On the other hand, the wax component filtered was weighed after air drying and drying in a vacuum drier at a pressure of 20 mmHg.

The composition (wt.%) and purity (wt.% of linear α-olefin in each fraction) of each fraction of α-olefin obtained by the above-described process and the composition of wax (wt.%) are shown in Table 4.

TABLE 4

| Catalyst Composition | Example 28 | | Example 29 | | Example 30 | | Example 31 | | Example 32 | | Example 33 | |
|---|---|---|---|---|---|---|---|---|---|---|---|---|
| $ZrCl_4$ (mmol) | 1.0 | | 1.0 | | 1.0 | | 1.0 | | 1.0 | | 1.0 | |
| $ZTP^1$ (mmol) | — | | — | | — | | — | | — | | — | |
| $DEAC^2$ (mmol) | 2.5 | | 2.5 | | 2.5 | | 2.5 | | 2.5 | | 2.5 | |
| $EADC^3$ (mmol) | — | | — | | — | | — | | — | | — | |
| $MDS^4$ (mmol) | 0.15 | | 0.4 | | 0.6 | | — | | — | | — | |
| $TP^5$ (mmol) | — | | — | | — | | 0.6 | | 1.2 | | — | |
| $AN^6$ (mmol) | — | | — | | — | | — | | — | | 0.6 | |
| $TU^7$ (mmol) | — | | — | | — | | — | | — | | — | |
| Al/Zr (mol/mol) | 2.5 | | 2.5 | | 2.5 | | 2.5 | | 2.5 | | 2.5 | |
| $CB^8$ (ml) | 250 | | 250 | | 250 | | 250 | | 250 | | 250 | |
| Yield (g) | 530 | | 162 | | 90 | | 535 | | 263 | | 540 | |
| Product | C (wt.%) | P (%) | C (wt.%) | P (%) | C (wt.%) | P (%) | C (wt.%) | P (%) | C (wt.%) | P (%) | C (wt.%) | P (%) |
| α-Olefin | | | | | | | | | | | | |
| $C_4$ | 1.7 | 100 | 3.3 | 100 | 5.6 | 100 | 1.7 | 100 | 2.4 | 100 | 2.0 | 100 |
| $C_6$ | 7.6 | 98 | 10.2 | 100 | 15.7 | 100 | 4.9 | 97 | 6.3 | 99 | 3.8 | 96 |
| $C_8$ | 10.3 | 96 | 16.8 | 99 | 19.9 | 99 | 9.4 | 93 | 13.2 | 97 | 7.0 | 95 |
| $C_{10}$ | 10.0 | 93 | 15.1 | 98 | 16.3 | 97 | 9.7 | 88 | 16.1 | 95 | 7.8 | 91 |
| $C_{12}$ | 9.8 | 90 | 13.2 | 98 | 12.6 | 96 | 10.3 | 85 | 15.9 | 93 | 9.0 | 88 |
| $C_{14}$ | 8.4 | 87 | 10.3 | 97 | 9.0 | 95 | 8.2 | 84 | 8.3 | 92 | 10.2 | 87 |
| $C_{16}$ | 7.6 | 85 | 8.2 | 96 | 7.4 | 95 | 7.6 | 83 | 7.6 | 90 | 8.0 | 86 |
| $C_{18}$ | 7.0 | 83 | 6.1 | 95 | 5.0 | 94 | 7.4 | 81 | 6.7 | 89 | 7.3 | 84 |
| $C_{20+}$ | 11.3 | 80 | 6.8 | 95 | 5.8 | 94 | 11.3 | 80 | 8.3 | 87 | 9.9 | 82 |
| Wax | 26.3 | — | 10.0 | — | 2.7 | — | 29.8 | — | 15.2 | — | 35.0 | — |

| Catalyst Composition | Example 34 | | Example 35 | | Example 36 | | C. Ex. 14 | | C. Ex. 15 | | C. Ex. 16 | |
|---|---|---|---|---|---|---|---|---|---|---|---|---|
| $ZrCl_4$ (mmol) | 1.0 | | 1.0 | | 1.0 | | 1.0 | | 1.0 | | — | |
| $ZTP^1$ (mmol) | — | | — | | — | | — | | — | | 1.0 | |
| $DEAC^2$ (mmol) | 2.5 | | 2.5 | | 5.0 | | 2.5 | | — | | 2.5 | |
| $EADC^3$ (mmol) | — | | — | | — | | — | | 2.5 | | — | |
| $MDS^4$ (mmol) | — | | — | | 0.5 | | — | | — | | — | |
| $TP^5$ (mmol) | — | | — | | — | | — | | — | | — | |
| $AN^6$ (mmol) | 1.2 | | — | | — | | — | | — | | — | |
| $TU^7$ (mmol) | — | | 0.6 | | — | | — | | — | | — | |
| Al/Zr (mol/mol) | 2.5 | | 2.5 | | 5.0 | | 2.5 | | 2.5 | | 2.5 | |
| $CB^8$ (ml) | 250 | | 250 | | 250 | | 250 | | 250 | | 250 | |
| Yield (g) | 252 | | 62 | | 316 | | 610 | | 60 | | — | |
| Product | C (wt.%) | P (%) | C (wt.%) | P (%) | C (wt.%) | P (%) | C (wt.%) | P (%) | C (wt.%) | P (%) | C (wt.%) | P (%) |
| α-Olefin | | | | | | | | | | | | |
| $C_4$ | 4.5 | 100 | 4.3 | 100 | 6.1 | 100 | 2.8 | 85 | 55.6 | 75 | No Reaction | " |
| $C_6$ | 6.3 | 99 | 12.1 | 100 | 13.9 | 99 | 6.8 | 78 | 22.1 | 55 | | " |
| $C_8$ | 10.3 | 98 | 12.4 | 100 | 15.4 | 96 | 8.4 | 77 | 14.8 | 27 | | " |
| $C_{10}$ | 12.0 | 96 | 9.9 | 100 | 10.8 | 92 | 9.0 | 75 | 4.5 | 12 | | " |
| $C_{12}$ | 15.1 | 94 | 7.5 | 99 | 9.2 | 90 | 8.2 | 73 | 2.6 | 3 | | " |
| $C_{14}$ | 14.3 | 93 | 6.0 | 99 | 6.8 | 89 | 6.2 | 71 | | | — | " |
| $C_{16}$ | 8.2 | 91 | 4.6 | 98 | 5.1 | 87 | 5.0 | 68 | 0.4 | — | | " |
| $C_{18}$ | 5.2 | 89 | 3.5 | 97 | 3.8 | 85 | 4.5 | 64 | | | — | " |
| $C_{20+}$ | 6.7 | 89 | 4.4 | 97 | 3.5 | 83 | 6.8 | 64 | | | — | " |

| Wax | 17.4 | — | 35.3 | — | 25.4 | — | 42.3 | — | — | — | " |

Notes:
[1] ZTP: Zirconium tatra(n-propoxide),
[2] DEAC: Diethylaluminum chloride,
[3] EADC: Ethylaluminum dichloride,
[4] MDS: Methyl disulfide,
[5] TP: Thiophene,
[6] AN: Aniline,
[7] TU: Thiourea,
[8] CB: Chlorobenzene

EXAMPLES 37–44 AND COMPARATIVE EXAMPLES 17–19

Preparation Example of Catalyst (Preparation of Catalyst Liquor)

Catalyst liquors were prepared in the same manner as in Examples 28 to 36 except that the zirconium compounds shown in Table 5 were used in amounts indicated in Table 5. Preparation Example of α-Olefins (Oligomerization of Ethylene)

α-Olefins were prepared in the same manner as in Example 28 to 36 except that the above-described catalyst liquors were used.

The same post-treatments as in Examples 28 to 36 were carried out.

The composition (wt. %) and purity (wt.% of linear α-olefin in each fraction) of each fraction of α-olefin obtained by the above-described process and the composition of wax (wt.%) are shown in Table 5.

TABLE 5

| Catalyst Composition | Example 37 | Example 38 | Example 39 | Example 40 | Example 41 | Example 42 |
|---|---|---|---|---|---|---|
| $ZrCl_4$ (mmol) | 1.0 | 1.0 | 1.0 | 1.0 | 1.0 | 1.0 |
| ZTP[1] (mmol) | — | — | — | — | — | — |
| DEAC[2] (mmol) | 2.5 | 2.5 | 2.5 | 2.5 | 2.5 | 2.5 |
| EADC[3] (mmol) | — | — | — | — | — | — |
| TBP[4] (mmol) | 0.4 | 0.3 | 0.25 | 0.4 | 0.3 | 0.25 |
| TOP[5] (mmol) | — | — | — | — | — | — |
| TPP[6] (mmol) | — | — | — | — | — | — |
| Al/Zr (mol/mol) | 2.5 | 2.5 | 2.5 | 2.5 | 2.5 | 2.5 |
| Benzene (ml) | 250 | 250 | 250 | 250 | 250 | 250 |
| Yield (g) | 50 | 137 | 432 | 32 | 112 | 441 |

| Product | C (wt. %) | P (%) | C (wt. %) | P (%) | C (wt. %) | P (%) | C (wt. %) | P (%) | C (wt. %) | P (%) | C (wt. %) | P (%) |
|---|---|---|---|---|---|---|---|---|---|---|---|---|
| α-Olefin | | | | | | | | | | | | |
| $C_4$ | 30.0 | 100 | 13.7 | 100 | 5.3 | 100 | 38.6 | 100 | 17.6 | 100 | 5.0 | 100 |
| $C_6$ | 30.6 | 100 | 19.8 | 99 | 12.7 | 99 | 24.2 | 100 | 19.3 | 99 | 11.2 | 99 |
| $C_8$ | 16.8 | 99 | 18.5 | 97 | 17.6 | 97 | 15.2 | 99 | 16.7 | 98 | 12.8 | 97 |
| $C_{10}$ | 8.5 | 98 | 12.8 | 96 | 14.6 | 95 | 7.8 | 99 | 13.2 | 97 | 11.3 | 96 |
| $C_{12}$ | 3.5 | 98 | 9.3 | 94 | 13.1 | 92 | 3.1 | 99 | 8.2 | 97 | 10.4 | 95 |
| $C_{14}$ | 2.8 | 97 | 7.9 | 93 | 9.7 | 89 | 2.5 | 98 | 5.7 | 96 | 9.7 | 94 |
| $C_{18}$ | 2.7 | 96 | 6.2 | 91 | 9.3 | 86 | 1.8 | 98 | 4.5 | 94 | 9.3 | 93 |
| $C_{18}$ | 1.8 | 96 | 4.8 | 90 | 7.8 | 84 | 1.8 | 97 | 3.8 | 93 | 8.5 | 92 |
| $C_{20+}$ | 1.6 | 95 | 5.0 | 90 | 8.0 | 82 | 1.6 | 97 | 4.3 | 93 | 9.6 | 90 |
| Wax | 1.7 | — | 2.0 | — | 1.9 | — | 3.4 | — | 6.7 | — | 12.2 | — |

| Catalyst Composition | Example 43 | Example 44 | C. Ex. 17 | C. Ex. 18 | C. Ex. 19 |
|---|---|---|---|---|---|
| $ZrCl_4$ (mmol) | 1.0 | 1.0 | 1.0 | 1.0 | — |
| ZTP[1] (mmol) | — | — | — | — | 1.0 |
| DEAC[2] (mmol) | 2.5 | 2.5 | 2.5 | — | 2.5 |
| EADC[3] (mmol) | — | — | — | 2.5 | — |
| TBP[4] (mmol) | — | — | — | — | — |
| TOP[5] (mmol) | — | — | — | — | — |
| TPP[6] (mmol) | 0.4 | 0.25 | — | — | — |
| Al/Zr (mol/mol) | 2.5 | 2.5 | 2.5 | 2.5 | 2.5 |
| Benzene (ml) | 250 | 250 | 250 | 250 | 250 |
| Yield (g) | 120 | 153 | 485 | 53 | 0 |

| Product | C (wt. %) | P (%) | C (wt. %) | P (%) | C (wt. %) | P (%) | C (wt. %) | P (%) | C (wt. %) | P (%) |
|---|---|---|---|---|---|---|---|---|---|---|
| α-Olefin | | | | | | | | | | |
| $C_4$ | 15.2 | 100 | 20.6 | 100 | 5.8 | 96 | 58.2 | 82 | No Reaction | |
| $C_6$ | 22.2 | 100 | 18.3 | 99 | 8.2 | 94 | 23.1 | 68 | " | |
| $C_8$ | 17.8 | 99 | 17.5 | 98 | 10.1 | 89 | 13.2 | 45 | " | |
| $C_{10}$ | 10.9 | 96 | 14.3 | 97 | 14.2 | 87 | 3.8 | 32 | " | |
| $C_{12}$ | 9.6 | 98 | 10.4 | 97 | 9.8 | 85 | 1.4 | 23 | " | |
| $C_{14}$ | 8.5 | 97 | 6.7 | 96 | 6.7 | 83 | — | | " | |
| $C_{16}$ | 7.8 | 96 | 5.3 | 95 | 5.2 | 80 | 0.3 | — | " | |
| $C_{18}$ | 4.7 | 95 | 3.7 | 94 | 3.8 | 78 | | | " | |
| $C_{20+}$ | 2.6 | 94 | 2.0 | 94 | 4.3 | 78 | — | | " | |

| | | | | | | | | |
|---|---|---|---|---|---|---|---|---|
| Wax | 0.7 | — | 1.2 | — | 31.9 | — | — | — |

Notes:
[1] ZTP: Zirconium tetra(n-propoxide),
[2] DEAC: Diethylaluminium chloride,
[3] EADC: Ethylaluminium dichloride,
[4] TBP: Tributylphosphine,
[5] TOP: Trioctylphosphine,
[6] TPP: Triphenylphosphine, While the invention has been described in detail and with reference to specific embodiments thereof, it will be apparent to one skilled in the art that various changes and modifications can be made therein without departing from the spirit and scope thereof.

What is claimed is:

1. A process for preparing a linear α-olefin having from 6 to 18 carbon atoms comprising polymerizing ethylene or an ethylene containing α-olefin in the presence of a catalyst consisting of a zirconium halide, an organoaluminum compound and a Lewis base in an inert solvent and terminating the polymerization by adding a catalyst deactivating agent to the resulting reaction mixture, wherein said catalyst contains a zirconium component comprising a zirconium halide represented by formula (I):

$$ZrX_aA_{4-a} \quad (I)$$

wherein X and A may be the same or different and each represents chloride, bromide atom or iodide and a is 0 or an integer of 1-4; an aluminium component comprising an alkylaluminum compound represented by formula (II):

$$AlR^1{}_{1.5}Q^1{}_{1.5} \quad (II)$$

wherein $R^1$ represents an alkyl group of 1-20 carbon atoms, Q represents chloride, bromide or iodide atom and said formula (II) may also be represented by $Al_2R^1{}_3Q^1{}_3$ and an alkylaluminum compound represented by formula (III):

$$AlR^2{}_bQ^2{}_{3-b} \quad (III)$$

wherein $R^2$ and $Q^2$ have the same meanings as $R^1$ and $Q^1$ above and b is an integer of 1-3; said catalyst being mixed at a molar ratio (Al/Zr) of said zirconium component and aluminum component of 3-15 and at a molar ratio $(AlR^1{}_{1.5}Q^1{}_{1.5}/AlR^2{}_bQ^2{}_{3-b})$ of the components represented by formulae (II) and (III) of 2-10; and said catalyst further contains at least one Lewis base selected from the group consisting of thiophene, methyl disulfide, thiourea triphenylphosphine and trioctylphosphine.

2. A process according to claim 1 wherein 0.005-5 mmols of the zirconium component, 0.02-15 mmols of the alkylaluminum compound and 0.02-20 mmols of the Lewis base are used per 250 ml of the inert solvent when the Lewis base is selected from group consisting of thiophene, methyl disulfide and thiourea.

3. A process according to claim 1, are used per 250 ml of the inert solvent when the is selected from the group consisting of triphenylphosphine and trioctylphosphine 0.01-5 mmols of the Lewis base.

4. A process according to claim 1 where the zirconium halide is zirconium tetrachloride and $R^1$ and $R^2$ are ethyl and $Q^1$ and $Q^2$ are chlorine.

5. A process according to claim 1 wherein the zirconium halide represented by the formula (I) is zirconium tetrachloride, the alkylaluminum represented by the formula (II) is ethylaluminum sesquichloride and the alkylaluminum represented by the formula (III) is triethylaluminum.

6. A process according to claim 1 further comprising the addition of at least one nitrogen compound selected from the group consisting of trimethylamine, triethylamine, ammonia gas, ammonia water and n-methylpiperidine prior to the addition of the catalyst deactivating agent.

* * * * *